United States Patent [19]

Kirwan, Jr.

[11] Patent Number: 5,089,002
[45] Date of Patent: Feb. 18, 1992

[54] DISPOSABLE BIPOLAR COAGULATOR

[75] Inventor: Lawrence T. Kirwan, Jr., Kingston, Mass.

[73] Assignee: Kirwan Surgical Products, Inc., Rockland, Mass.

[21] Appl. No.: 603,257

[22] Filed: Oct. 29, 1990

Related U.S. Application Data

[63] Continuation of Ser. No. 344,607, Apr. 6, 1989, abandoned.

[51] Int. Cl.⁵ .............................................. A61B 17/36
[52] U.S. Cl. ........................................ 606/50; 606/45
[58] Field of Search ..................... 128/783, 784, 800; 606/41, 43, 44, 45, 48, 49, 50

[56] References Cited

U.S. PATENT DOCUMENTS

| | | | |
|---|---|---|---|
| 4,170,234 | 10/1979 | Graham | 606/49 |
| 4,476,862 | 10/1984 | Pao | 606/50 |
| 4,483,338 | 11/1984 | Bloom et al. | 606/50 |
| 4,548,207 | 10/1985 | Reimels | 606/50 |
| 4,593,691 | 1/1986 | Lindstrom et al. | 606/49 |
| 4,688,569 | 8/1987 | Rabinowitz | 606/49 |
| 4,872,454 | 10/1989 | DeOliveira et al. | 606/45 |

*Primary Examiner*—Max Hindenburg

[57] ABSTRACT

This inventon is directed at a disposable bipolar coagulator which includes a coaxial conductor with a unitary housing. The coaxial conductor includes an outer conductor, an inner conductor and a circumferential insulator. The coaxial conductor is formed by passing the inner conductor through the outer conductor after the insulator has been formed over the inner conductor. The coaxial conductor thus formed includes three terminal ends. The first and second terminal ends of the coaxial conductor are formed in spaced, parallel relation to each other. A first connector pin is coupled to the first terminal end and a second connector pin is coupled to the second termianl end. The unitary housing is molded over the electrical sub-assembly formed by the coupling of the coaxial conductor and the connector pins forming the coagulator.

4 Claims, 1 Drawing Sheet

DISPOSABLE BIPOLAR COAGULATOR

This is a continuation of copending application Ser. No. 07/334,607 filed on Apr. 6, 1989, now abandoned.

BACKGROUND OF THE INVENTION

1. Field of the invention

This invention relates to bipolar coagulators having unitary housings.

SUMMARY OF THE INVENTION

The invention disclosed herein is directed at a disposable bipolar coagulator which includes a coaxial conductor and an insulating housing. The insulating housing is formed of a deformable plastic in one unitary body which circumscribes a portion of the coaxial conductor. The coaxial conductor includes an inner and an outer conductor with the outer conductor having a first end and the inner conductor having a second end. The first and second ends in spaced, parallel relation to each other. A circumferential insulating material is formed over a portion of the inner conductor. First and second connector pins are coupled to the first and second ends of the inner and outer conductors, respectively. The coupling of the coaxial conductor with the connector pins forms an electrical sub-assembly and the insulating housing is formed in one unitary body over this sub-assembly. A portion of the first and second connector pins and a portion of the coaxial conductor extend from the insulating housing.

BRIEF DESCRIPTION OF THE DRAWINGS

Further details are explained below with the help of the example(s) illustrated in the attached drawings in which.

DESCRIPTION OF THE PREFERRED EMBODIMENT

Figure 1:
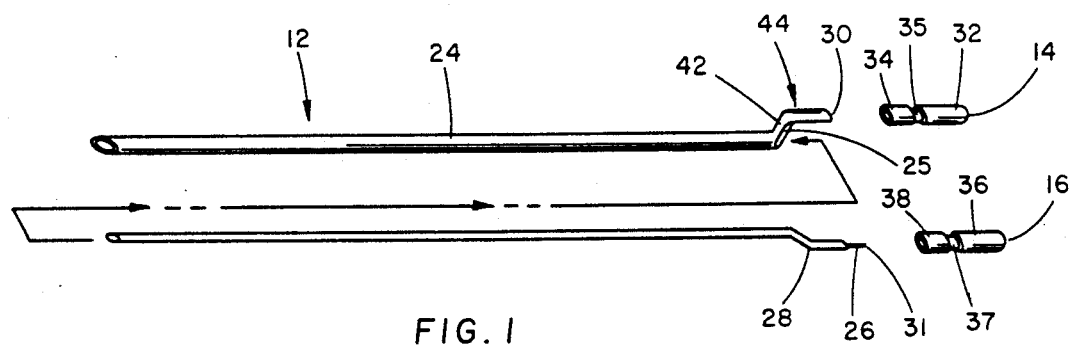
FIG. 1 is an exploded view of the electrical sub-assembly according to the present invention.

Shown in the drawings is a disposable bipolar coagulator 8. The coagulator 8 includes an outer housing 10, a coaxial conductor 12, and first and second connector pins 14 and 16.

Figure 2:
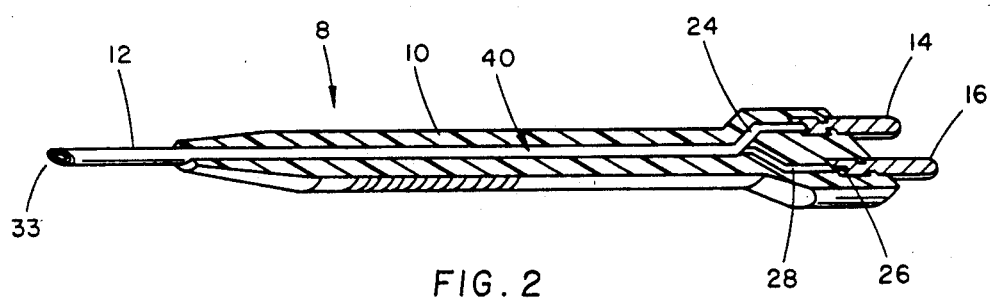
FIG. 2 is a cross sectional view of the coagulator showing the placement of the electrical sub-assembly, shown in FIG. 1, within the unitary housing.

As illustrated in FIGS. 1 and 2, the coaxial conductor 12 comprises an outer conductor 24, an inner conductor 26 and a first terminal end 33. The inner conductor 26 and the outer conductor 24 are separated for a substantial portion of their length by an insulator 28. The outer conductor 24 comprises a length of stainless steel tubing with a first end 30 remote from the terminal end 33. A first bend 42 and a second bend 44 are formed in the outer conductor 24 in opposed direction to each other, in close proximity to the first end 30 with the first bend 42 positioned further away from the first end 30 than the second bend 44. The first and second bends 42 and 44 are formed at an angle to the longitudinal axis of the conductor 24 and an aperture 25 is ground into the outer conductor 24 between the bends 42, 44 as shown in FIG. 1. The inner conductor 26 comprises a length of stainless steel wire which includes a second end 31 separated from the first terminal end 33.

Figure 4:
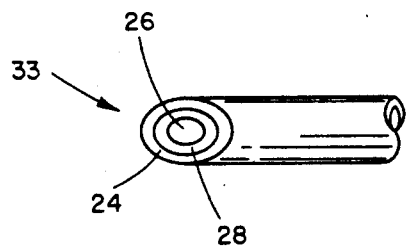
FIG. 4 is a cut-away view of the first terminal end showing the placement of the inner conductor and insulator within the outer conductor.

As illustrated in FIG. 1, the coaxial conductor 12 may be formed by passing the terminal end, of the sub-assembly of the inner conductor 26 and the circumferential insulator 28, remote from the end 31 through the aperture 25 and through the outer conductor 24. When the inner conductor 26 has been positioned within the outer conductor 24 the second end 31, of the inner conductor 26, will be spaced from and in parallel relation to the first end 30 of the outer conductor 24. As illustrated in FIG. 4, the first terminal end 33 may be beveled by grinding it down to an angle or it may be left straight, conical or flat sided as required.

The connector pin 14, which may be formed in one integral section from stainless steel wire, includes a body portion 32, an annular channel 35 and a sleeve portion 34. The body portion 32 is generally cylindrical while the sleeve portion 34 is tubular. Similarly, the connector pin 16, which may also be formed in one integral section of stainless steel wire, includes a body portion 36, an annular channel 37 and a sleeve portion 38. The body portion 36 is generally cylindrical while the sleeve portion 38 is tubular.

The first connector pin 14 is coupled to the outer conductor 24 by inserting the end 30, of the outer conductor 24, into the sleeve portion 34. The sleeve portion 34 is crimped fastening the end 30 and the connector pin 14 together. The second connector pin 16 is coupled to the inner conductor 26 by inserting the end 31, of the inner conductor 26, into the sleeve portion 38. The sleeve portion 38 is crimped fastening the end 31 and the connector pin 16 together. The connection of the outer conductor 24 and the inner conductor 26 with the connector pins 12 and 14 forms an electrical sub-assembly 40.

Figure 3:
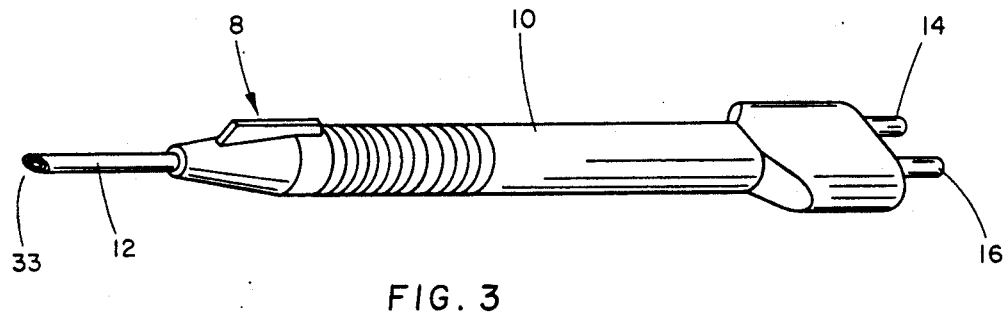
FIG. 3 is a side elevational view of the coagulator, shown in FIG. 2, showing the placement of the first and second connector pins and the first terminal end.

As illustrated in FIG. 3, the outer housing 10 is generally cylindrical in configuration and is formed in one unitary section over the sub-assembly 40 by placing a portion of the sub-assembly 40 in an injection mold and injecting a suitable plastic in a manner well known in the art. The molding apparatus leaves a portion of the connector pins 14 and 16 and a portion of the terminal end 33 exposed. The housing 10 formed in this manner electrically insulates the inner and outer conductors 26 and 24 from accidental shorting.

Electrically the outer conductor 24 may carry a positive current while the inner conductor 26 carries a negative current. The disposable bipolar coagulator 8 is used for manipulating tissue and at the surgeon's desire coagulating or desiccating the tissue by a voltage from an electrosurgical generator (not shown) connected to the coagulator 8. The electrosurgical generator is connected to the connector pins 14 and 16 by a standard socket assembly as well known in the art.

What I claim is:

1. A disposable bipolar coagulator comprising a coaxial conductor and an insulating housing; the insulating housing being formed of a deformable plastic in one unitary body which circumscribes a portion of the coaxial conductor; the coaxial conductor including an inner and an outer conductor; the outer conductor having a prime end; the inner conductor having a secondary end; the prime end having a first terminal end and the secondary end has a terminal end, the prime end has a first bend formed therein directed away from the inner conductor and the prime end has a second bend formed therein which positions the first terminal end in spaced parallel relation to the remaining major portion of the outer conductor; the secondary end of the inner conductor is also bent twice to place its terminal end in spaced parallel relation to the first terminal end; a through aperture is formed in the outer conductor in close proximity to the first bend and through which the inner conductor is passed, the first and second ends being in spaced parallel relation to each other; the inner and outer conductors formed of an electrically conductive material; a circumferential insulating material being formed over a portion of the inner conductor; the insulating housing having first and second free terminal ends; a portion of the coaxial conductor extending from the second free terminal end.

2. The disposable bipolar coagulator as set forth in claim 1 further comprising a first connector pin and a second connector pin; the first connector pin including a first body portion and a first sleeve portion; the second connector pin including a second body portion and a second sleeve portion; the first connector pin is attached to the outer conductor; the second connector pin is attached to the inner conductor; the first and second connector pins being formed of an electrically conductive material.

3. The disposable bipolar coagulator as set forth in claim 2 wherein the first sleeve portion is positioned over the first end of the outer conductor; the first sleeve portion being crimped over the first end of the outer conductor; the second sleeve portion is positioned over the second end of the inner conductor; the second sleeve portion being crimped over the second end of the inner conductor.

4. The disposable bipolar coagulator as set forth in claim 3 wherein the connection of the coaxial conductor with the first and second connector pins forms an electrical sub-assembly; the insulating housing being formed in one unitary body over the electrical sub-assembly; a portion of the first and second connector pins extending from the first terminal end of the insulating housing.

* * * * *